United States Patent [19]

Ishikawa

[11] Patent Number: 5,322,796
[45] Date of Patent: Jun. 21, 1994

[54] METHOD OF DISCRIMINATING A KIND OF NUCLEIC ACIDS BASES

[75] Inventor: Mitsuru Ishikawa, Hamamatsu, Japan

[73] Assignee: Hamamatsu Photonics K.K., Shizuoka, Japan

[21] Appl. No.: 968,868

[22] Filed: Nov. 2, 1992

[30] Foreign Application Priority Data

Oct. 31, 1991 [JP] Japan .................. 3-286290

[51] Int. Cl.$^5$ .................. G01N 33/00; C12Q 1/68
[52] U.S. Cl. .................. 436/94; 436/96; 435/6; 935/77
[58] Field of Search .................. 436/96, 94; 536/27; 435/6; 935/77

[56] References Cited

U.S. PATENT DOCUMENTS

| | | | |
|---|---|---|---|
| 4,959,309 | 9/1990 | Dattagupta et al. | 435/6 |
| 4,962,020 | 10/1990 | Tabor et al. | 435/6 |
| 4,962,037 | 10/1990 | Jett et al. | 435/6 |
| 5,171,534 | 12/1992 | Smith et al. | 422/82.05 |

OTHER PUBLICATIONS

"The Excited Sttes of Nucleic Acids", Eisinger, Photochemicstry and Photobiology, 1968, vol. 7, pp. 597–612.
"Single-Molecule Detection of Rhodamine 6G in Ethanolic Solutions Using Continuous Wave Laser Excitation", Soper et al., Anal. Chem. 1991, 63, 432–437.
"Single Pentacene Molecules Detected by Fluorescence Excitation in a p-Terphenyl Crystal", Orrit et al., Physical Review Letters, vol. 65, No. 21, 1990.
"Detection and N Spectroscopy of Single Pentacene Molecules in a p-Terphenyl Crystal by Means of Fluorescense Excitation", Ambrose et al., J. Chem. Phys., 95 (10), 1991.
"A Single-Photon Sensitive Synchroscan Streak Camera for Room Temperature Picosecond Emission Dynamics of Adenine and Polyadenylic Acid", Kobayashi et al., IEEE Journal of Quantum Electronics, vol. QE-20, No. 12, 1984.
"Excited States of Nucleotides", Eisinger et al., Basic Principles in Nucleric Acid.
"The Fluorescence of Adenine, The Effects of Solvent and Temperature on the Quantum Yield", Eastman et al., Photochemistry and Photobiology, 1968, vol. 7, pp. 189–201.
"Characterization of Fluorescence-Labelled DNA by Time-Resolved Fluorescence Spectroscopy", Seidel et al., Physikalisch Chemnisches Institut, Universitat Heidelberg.

Primary Examiner—James C. Housel
Assistant Examiner—N. Bhat
Attorney, Agent, or Firm—Cushman, Darby & Cushman

[57] ABSTRACT

A method for discriminating four kinds of nucleic acid bases of DNA at high speed by utilizing chromophores intrinsic to DNA. The sample is added to a polar glassy solvent. Then the temperature of the glassy solution is reduced. A $(n, \pi^*)$ quencher is then added as a fluorescence intensifying reagent to the solution. The solution is then irradiated with an excitation light of UV laser beams thereto. The lifetimes of fluorescence from the sample are measured and used to discriminate the nucleic acid bases of DNA.

4 Claims, 15 Drawing Sheets

| | FLUORESCENCE LIFETIME (ps.) | RATIO OF COMPONENT (%) |
|---|---|---|
| A | 377 | 76.8 |
|   | $5.2 \times 10^3$ | 23.2 |
| T | 322 | 69.0 |
|   | $2.8 \times 10^3$ | 31.0 |
| G | $1 \times 10^3$ | 32.6 |
|   | $5.5 \times 10^3$ | 67.4 |
| C | 219 | 81.0 |
|   | $1.8 \times 10^3$ | 19.0 |

$\begin{pmatrix} H_2O:CH_3OH = 1:1 \\ 77K \\ \text{ADDITION OF 0.1N} \\ \text{HYDROLIC ACID} \end{pmatrix}$

FIG. IC
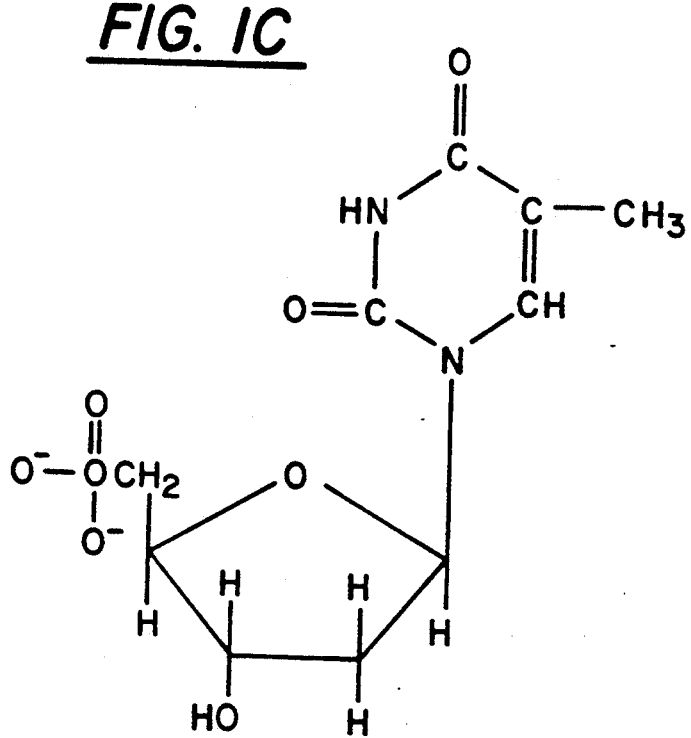
FIG. ID
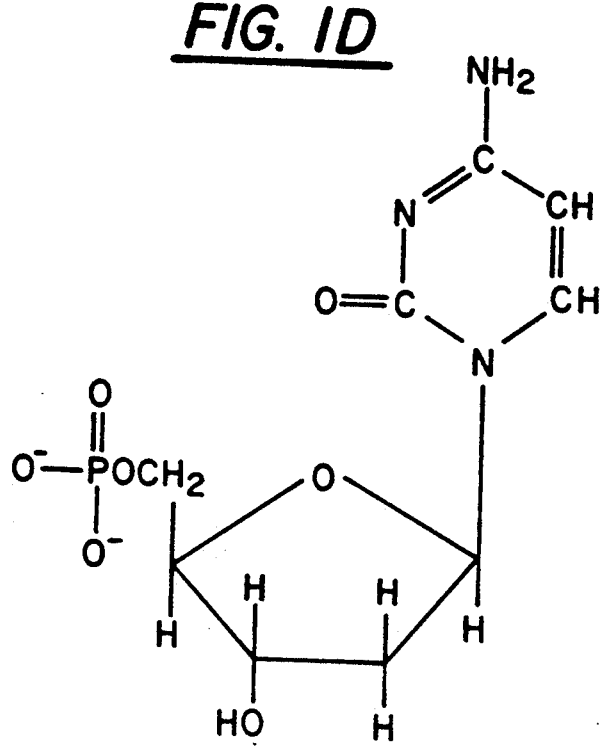

FIG. 5

| FLUORESCENCE LIFETIME (ps) | | RATIO OF COMPONENT (%) |
|---|---|---|
| A | 500 | 67.5 |
|   | $3 \times 10^3$ | 26.8 |
| T | 490 | 47.6 |
|   | $2.8 \times 10^3$ | 50.1 |
| G | 228 | 62.0 |
|   | $2.4 \times 10^3$ | 24.7 |
|   | $8.4 \times 10^3$ | 13.3 |
| C | 365 | 77.6 |
|   | $1.9 \times 10^3$ | 21.1 |

$\left( \begin{array}{l} H_2O : CH_3OH = 1:1 \\ 77K \end{array} \right)$

FIG. 7

| TEMPERATURE(K) | exp(-ΔE/RT) | kexp(-ΔE/RT) $_{(sec^{-1})}$ |
|---|---|---|
| 298 | $7.2 \times 10^{-4}$ | $7.2 \times 10^{19}$ |
| ⋮ | ⋮ | ⋮ |
| 218 | $4.9 \times 10^{-5}$ | $4.9 \times 10^{9}$ |
| ⋮ | ⋮ | ⋮ |
| 150 | $5.7 \times 10^{-7}$ | $5.7 \times 10^{7}$ |
| 120 | $1.6 \times 10^{-8}$ | $1.6 \times 10^{6}$ |
| 100 | $4.3 \times 10^{-10}$ | $4.3 \times 10^{4}$ |
| 77 | $6.8 \times 10^{-13}$ | 68 |

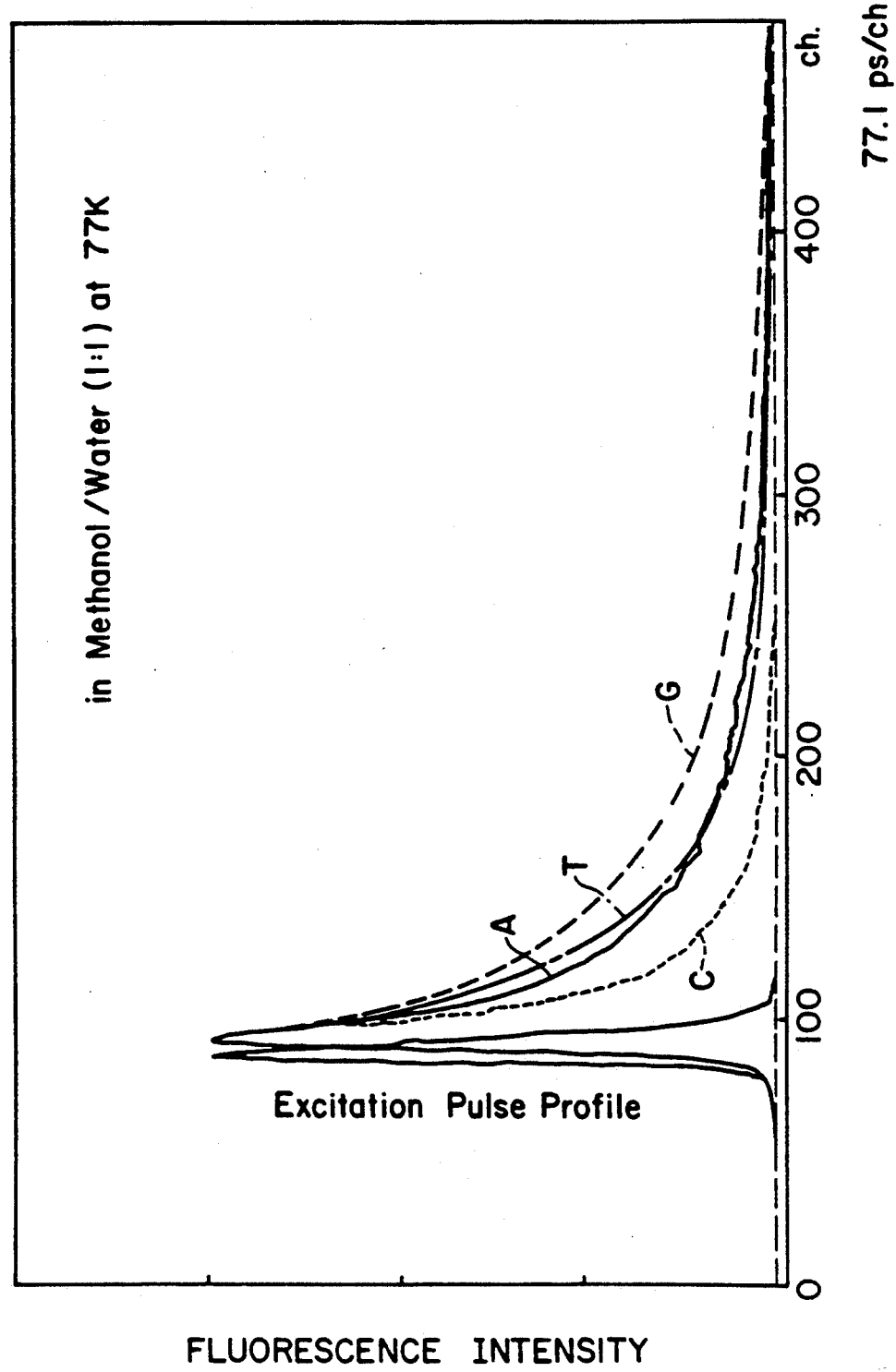

FIG. 9A

| | FLUORESCENCE LIFETIME (ps.) | RATIO OF COMPONENT (%) |
|---|---|---|
| A | 377<br>$5.2 \times 10^3$ | 76.8<br>23.2 |
| T | 322<br>$2.8 \times 10^3$ | 69.0<br>31.0 |
| G | $1 \times 10^3$<br>$5.5 \times 10^3$ | 32.6<br>67.4 |
| C | 219<br>$1.8 \times 10^3$ | 81.0<br>19.0 |

$\begin{pmatrix} H_2O:CH_3OH = 1:1 \\ 77K \\ \text{ADDITION OF 0.1N} \\ \text{HYDROLIC ACID} \end{pmatrix}$

FIG. 9B

| KIND OF NUCLEIC ACID | AVERAGE LIFETIME AT 77K | |
|---|---|---|
| | METHANOL/WATER | METHANOL/0.1N HCL |
| GUANINE (G) | 1.84 ns | 4.04 ns |
| CYTOSINE (C) | 0.84 ns | 0.53 ns |
| ADENINE (A) | 1.72 ns | 1.49 ns |
| THYMINE (T) | 1.66 ns | 1.09 ns |

ABSORPTION SPECTRA

ABSORPTION SPECTRA

METHOD OF DISCRIMINATING A KIND OF NUCLEIC ACIDS BASES

BACKGROUND OF THE INVENTION

1. Field of the Invention

This invention relates to a method for discriminating a kind of nucleic acid bases of DNA.

2. Related Background Art

As shown in FIGS. 1A–1D, DNA (deoxyribonucleic acid) is a copolymer of four kinds of deoxynucleotides, which are shown in FIGS. 2A–2D, i.e., deoxyadenylic acid (shown in FIG. 1A), deoxyguanylic acid (shown in FIG. 1B), deoxythymidylic acid (shown in FIG. 1C), and deoxycytidylic acid (shown in FIG. 1D). These deoxynucleotides have at the base sites of their respective deoxyriboses an adenine, a guanine, a thymine, or a cytosine, which are nucleic acid bases. A sequence of these deoxynucleotides is intrinsic to a gene.

Conventionally in sequencing these deoxynucleotides, a DNA chain is labeled using a radioactive isotope (R.I.) or a fluorescent dye. The conventional method is disclosed in U.S. Pat. No. 4,962,037. But this method needs a preparatory treatment of separately adding a fluorescent dye, etc.

In view of this, discriminating methods using the chromophores of DNA are used. As a typical example of these methods, a method using a solution of DNA in a water/methanol solvent with a ratio of 1:1 is described in "Basic Principles in Nucleic Acid Chemistry", Vol. I, Academic Press (1974), p. 322~328. In this method, a temperature of this solution is lowered to 77K, and then UV laser beams are irradiated to the sample solution by a secondary higher harmonic generator. By these laser beams directed to electrons of the respective chromophores of A (adenine), T (thymine), G (guanine), C (cytosine), four kinds of nucleic acid bases of each of DNAs are discriminated from each molecule flowing one after another in the above-mentioned solution. The reference discloses that the irradiation of laser beams as excitation light at a temperature below room temperature much improves quantum yields of the nucleic acid bases in comparison with yields at room temperature.

The solvent comprises a the mixture of water and methanol because, when water is used alone, cubical expansions of the water take place at low temperatures, breaking the container. Usually alcohol is added to water for the prevention of volume expansion at low temperatures, and, additionally, causes the solvent to be transparent and vitreous.

FIGS. 3A–3D show spectra of the fluorescence and phosphorescence emitted from the solution using the above-described method in A, T, G and C, respectively. As shown, all the nucleic acid bases have peaks of fluorescence near a wavelength of 325 nm. A and G have spectra having high peaks near 400 nm. These are phosphorescence spectra, and the lifetimes of the respective phosphorescence are of A and G 2.7 seconds, and 1.6 seconds. By their respective phosphorescence lifetimes, A and G can be discriminated from each other. T and C, which emit no phosphorescence, are measured in terms of lifetimes of fluorescence. FIG. 10 shows the lifetimes of fluorescence of the four kinds of nucleic acid bases. In FIGS. 4A–4D, fluorescence intensity is taken on the vertical axis, and lifetime of fluorescence is taken on the horizontal axis. 1 ch on the horizontal axis is equal to 77 psce. The sharp peaks around 100 ch show excitation light, and the blunt extinction curves of FIGS. 4A–4D respectively show the fluorescence from the nucleic acid bases A, T, G and C. In comparison with the fluorescence lifetime of T and that of C, which cannot be discriminated by phosphorescence, it is apparent that there is a difference in the extinction curve therebetween. Accordingly T and C can be discriminated from each other by fluorescence lifetime.

This method can be used to discriminate A from G by phosphorescence lifetime. However, but taking into account ultra-high speed sequencing, (at a speed at which one base can be identified per 1 second at worst), the respective phosphorescence lifetimes of A and G are too long to be used as a parameter for the discrimination of the nucleic acid bases.

The method discrimination by phosphorescence lifetime cannot be used for T or C, because T and C emit no phosphorescence. Accordingly T and C have to be discriminated from each other using respective fluorescence lifetimes. As a result, a problem exists in the current art that the nucleic acid bases contained in DNA cannot be discriminated from one another efficiently at ultra-high speed.

FIG. 5 shows relationships between fluorescence lifetimes of long lifetime components and ratios of the components. But as shown in FIG. 5, there are cases in which the discrimination is difficult, and made possible only by comparison of fluorescence lifetimes. Based on the long lifetime components, the ratio of the fluorescence lifetime 365 ps of C is 77.6%, which can be apparently discriminated from the other three nucleic acids A, T, G. But it is difficult to discriminate A, T, G by long lifetime components. Furthermore, even if G can be discriminated, it will be difficult to discriminate A from T.

SUMMARY OF THE INVENTION

In view of these problems in the art, an object of this invention is to provide a method of discriminating a kind of nucleic acid base at ultra-high speed without any pre-treatment addition of fluorescence dye to the nucleic acid bases.

A discriminating method according to this invention comprises the steps of: adding a sample including any nucleic acid to a polar vitreous solvent; cooling the same at very low temperature, adding a fluorescence intensifying agent to the vitreous solution and irradiating an excitation light thereto, measuring lifetimes of fluorescence from the solution; and discriminating each kind of the nucleic acid bases included in the sample, based on measured lifetimes of fluorescence from the vitreous solvent.

The vitreous (glassy) solvent is a polar solvent wherein the nucleic acid bases are soluble therein, which are polar molecules, such as alcohol, a mixed liquid of alcohol and water, a mixed liquid of alcohol and ether or ketone, etc. It is preferable that the fluorescence intensifying agent is a strong acid having no absorption spectrum in a wavelength range of the excitation light.

According to this invention, a fluorescence intensifying agent of (n, $\pi^*$) quencher is added to a sample solution at a low temperature, whereby differences in fluorescence lifetime can therefore be made readily distinguished.

A strong acid having no absorption spectrum in a wavelength range of the excitation light is used as the fluorescence intensifying agent. As a result protons are added to non-bonding electron pairs of the nucleic acid bases, whereby (n, $\pi^*$) states can be extinguished.

Changes of the electron state of the sample solution due to the addition of (n, $\pi^*$) quencher, for example, 0.1N hydrochloric acid are explained as follows. In the case where A and G are in a mixed solvent (77K) of a polar vitreous solution, for example, neutral or alkaline water and alcohol, the energy level of the single state (S), in which the electron spins are anti-parallel, and that of the triplet state (T), in which the electron spins are parallel, are on a level higher than their respective (n, $\pi^*$) state (FIG. 6A). When light is irradiated to the sample solution, electrons in the ground state are excited to the lowest single state ($\pi$, $\pi^*$). In accordance with the El-Sayed rule, inter system crossing from the $S_1$ ($\pi$, $\pi^*$) to the higher excited triplet state $T_2$ (n, $\pi^*$) tends to take place. The electrons in $T_2$ (n, $\pi^*$) state transit to the lowest excited triplet state $T_1$(n, $\pi^*$) due to the internal conversion, and when they transit further to the ground state, they emit phosphorescence. But the addition of a (n, $\pi^*$) quencher, for example, hydrochloric acid of 0.1N, to the sample solution, H$^+$s dissociated in the solution are added to non-bonding electron pairs in the n orbitals of the nucleic acid bases, and then the S2(n, $\pi^*$) state and the T2(n, $\pi^*$) state are extinguished (FIG. 6B). Accordingly inter system crossing is blocked, and the emission of phosphorescence is diminished.

In the case of nucleic acid base A, it is considered that, because of an equilibrium constant of the acid-base reaction in which non-bonding electron pairs of a chromophore combine with H$^+$s, the electron state of the sample solution with a (n, $\pi^*$) quencher added, for example, hydrochloric acid of 0.1N, has the mixed states as shown FIGS. 6A and 6B. Accordingly the emission of phosphorescence cannot be completely suppressed, but a small increase of fluorescence ratio to phosphorescence is obtained.

In the cases of nucleic acid bases T and C, as shown in FIG. 6C, $T_2$(n, $\pi^*$) state is on a higher level than $S_1(\pi, \pi^*)$ state. Accordingly no effective inter-system crossing through $T_2$(n, $\pi^*$) state takes place, and the emission of phosphorescence is small. Consequently, even with the addition of a (n, $\pi^*$) quencher, for example, hydrochloric acid of 0.1N to the sample solution, no phosphorescence is emitted because $T_2$(n, $\pi^*$) state does not originally contribute to the inter-system crossing from the $S_1(\pi, \pi^*)$ state, and the quenching is not effective.

Next, the fluorescence and the phosphorescence yields of the four kinds of nucleic acid bases, and temperature dependence of fluorescence lifetimes thereof, are briefly explained as follows. Generally, a fluorescence yield $\Phi_f$ is given by the following Formula 1.

$$\Phi_f = \frac{K_f}{K_f + K_{ISC}(\text{or } K_{ISC'}) + K_{IC} + K\exp(-\Delta E/RT)} \quad \text{[Formula 1]}$$

Generally a fluorescence lifetime $\tau_f$ is given by the following Formula 2.

$$\tau_f = \frac{1}{K_f + K_{ISC}(\text{or } K_{ISC'}) + K_{IC} + K\exp(-\Delta E/RT)} \quad \text{[Formula 2]}$$

In the above-described formulas, kf represents a speed constant of the fluorescence; KIC, a rate constant of an internal conversion independent of a temperature; KISC, a rate constant for cases where $T_2$(n, $\pi^*$) energy level contributes to an inter-system crossing; KISC', a rate constant for cases where $T_2$ (n, $\pi^*$) energy level does not contribute to an inter-system crossing; and Kexp($-\Delta E/RT$), a rate constant for an internal conversion dependent on a temperature. It is experimentally known that the temperature dependent rate is of an exp($-\Delta E/RT$) form, and $\Delta E$ represents activation energy, and R is a gas constant. FIG. 7 shows results given by replacing the respective speed constants and the activation energy assuming reasonable values, and shows changes of the temperature corresponding to values of Kexp($-\Delta/RT$). As shown there, since the fluorescence yield $\Phi f$ significantly decreases at temperatures higher than 150 K, it is preferable to measure the fluorescence lifetime at a temperature below 150K. Below 100K, Kexp($-\Delta E/RT$) is sufficiently negligible in comparison with the other rate constants. An arbitrary temperature below 100K may be used for increasing the fluorescence yield $\Phi_f$.

The present invention will become more fully understood from the detailed description given hereinbelow and the accompanying drawings which are given by way of illustration only, and thus are not to be considered as limiting the present invention.

The further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A–1D show molecular structures of deoxynucleotides in DNA, respectively;

FIG. 5 is a table of fluorescence lifetime of components and ratios of the components without the addition of a (n,$\pi^*$) quencher;

FIG. 7 shows the relationship between temperatures and rate constants of the temperature-dependent internal conversion in the single state;

FIG. 8B shows fluorescence decay curves of the samples to which quencher is not added;

FIG. 9A shows fluorescence lifetime components, and ratios of the components obtained by the method for discriminating nucleic acid bases according to this invention;

FIG. 9B shows average fluorescence lifetimes corresponding to A, T, G and C obtained from the experimental results shown in FIG. 8A and FIG. 8B.

DETAILED DESCRIPTION OF THE INVENTION

The nucleic acid bases discriminating method according to one example of this invention will be explained below.

First, four samples respectively including DNA bases A, T, G and C were prepared. Concretely, the four kinds of DNA bases were used as supplied (Yamasa Syoyu): disodium salt of: deoxy adenosine 5'-monophosphate (dAMP), deoxy guanosine 5'-monophosphate (dGMP), deoxy thymidine 5'-monophosphate (dTMP), and deoxy cytidine 5'-monophosphate (dCMP). All the bases were dissolved in 0.1N HCl (ca. $4 \times 10^{-5}$M) mixed with methanol (Dojin Luminasol). The ratio of mixing was 1:1 by volume. The concentration of each base was $2.5 \times 10^{-5}$ mol/liter in each of the samples. Next the temperature of each of the solvents was decreased to 77K. Next, UV beams irradiated the cooled solvent and the fluorescence intensity from the solvent due to the U.V. radiation was detected in each of the four samples by using a picosecond time-resolved fluorometer, for example, as shown in the reference titled as "Single-Photon Sensitive Synchroscan Streak Camera for Room Temperature Picosecond Emission Dynamic of Adenine and Polyadenylic Acid" in IEEE Journal of Quantum Electronics. Vol. QE-20, No. 12 December 1984. Concretely, the picosecond time-resolved fluorometer was composed of an exiting light source and a detector. The light source was a mode-locked and cavity-dumped fluorescein 548 dye laser (Spectra-Physics 375B and 344) synchronously pumped by a mode-locked cw Ar+ laser (Spectra-Physics 2030). The detector was a synchroscan streak camera (Hamamatsu C1587 equipped with a M2171 synchroscan unit for 4 MHz operation) coupled with a polychromator (Jobin-Y von HR320, 150 grooves/mm). A second harmonic generation was carried out by means of a 8 mm thick $\beta$-Ba B$_2$O$_4$(Type 1,51°) crystal. Picosecond pulses at the repetition rate of 4 MHz, having an average power of ca. 1.5 mW at 270 nm, were used to excite four kind of DNA bases. The fluorescence photons from the DNA bases were detected at a right angle to a vertically polarized exciting laser beam without a polarizer. Sample cuvettes (4 mm in diameter) and a Dewar vessel for liquid nitrogen were made of fluorescence-free quartz.

Figure 1A:
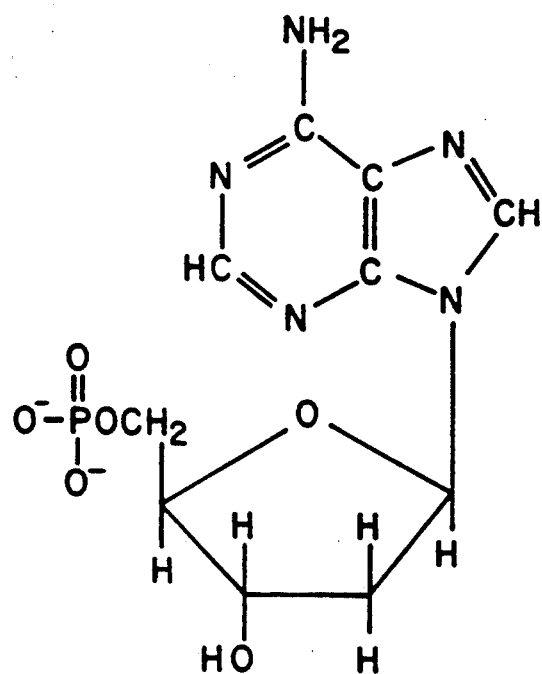
Figure 1B:
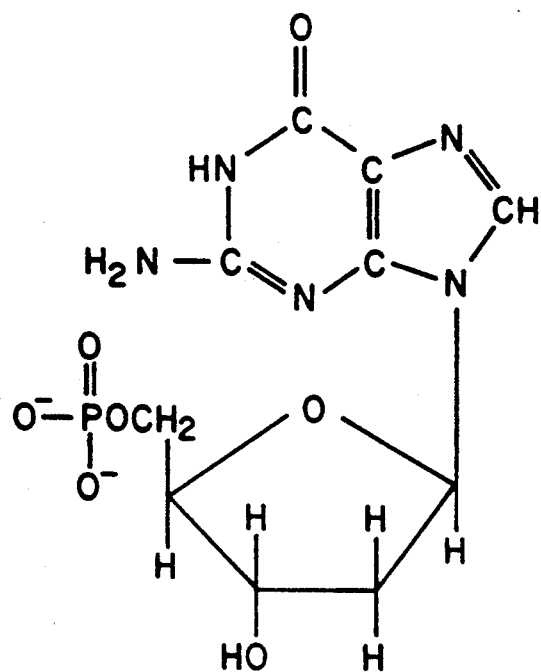
Figure 2C:
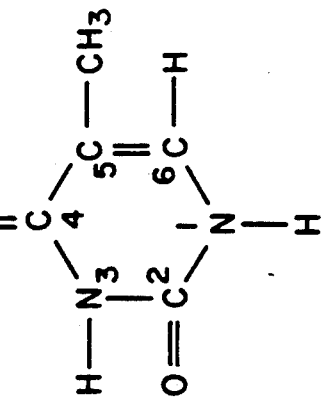
FIGS. 2A–2D show molecular structures of DNA and nucleic acid bases, respectively.
Figure 2D:
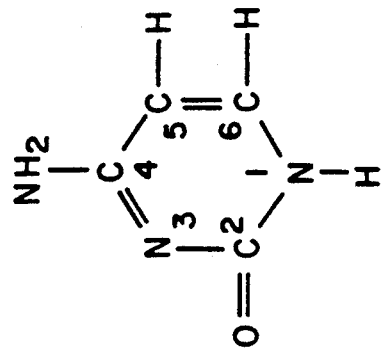
Figure 2A:
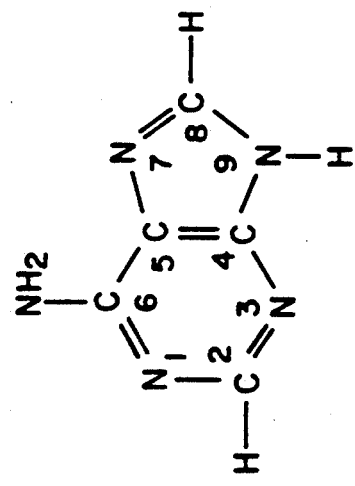
Figure 2B:
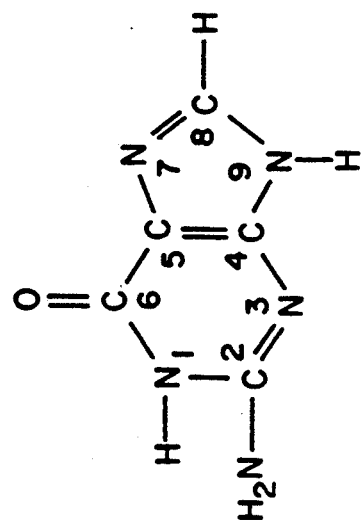
Figure 3A:
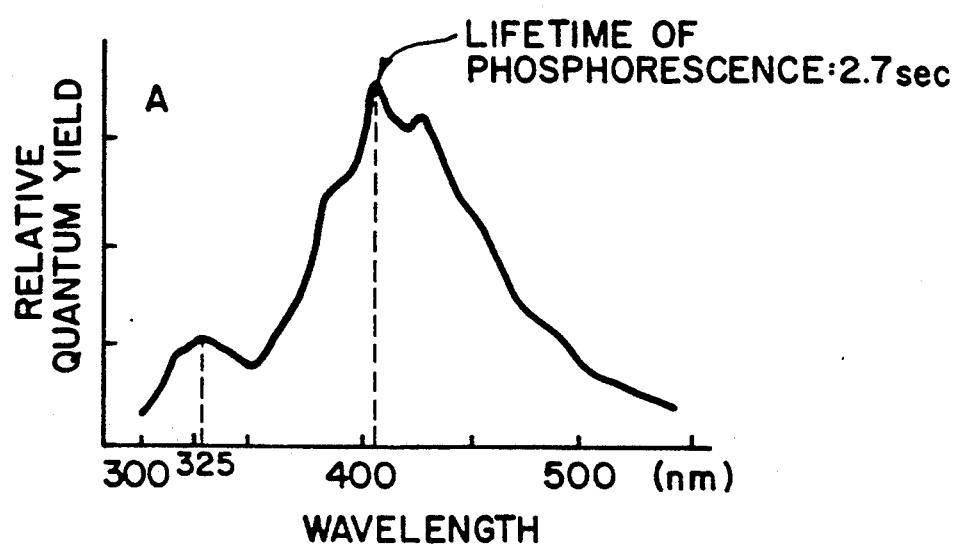
FIGS. 3A–3D are fluorescence and phosphorescence spectra without the addition of a (n, $\pi^*$) quencher.
Figure 3B:
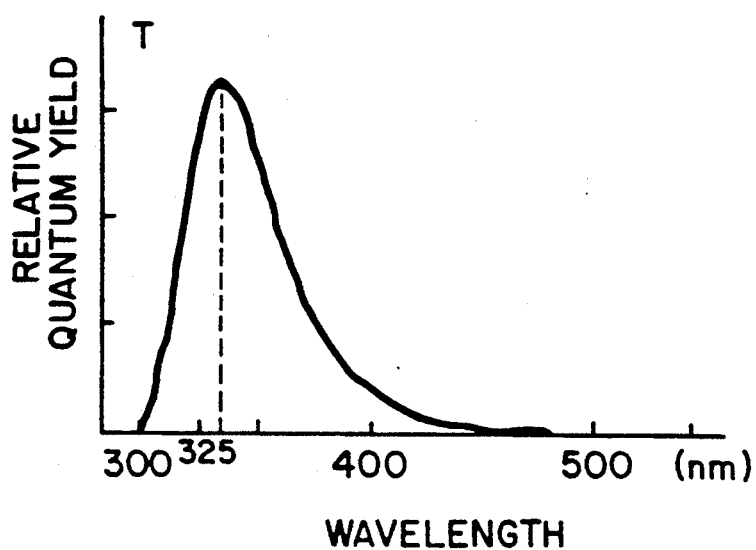
Figure 3C:
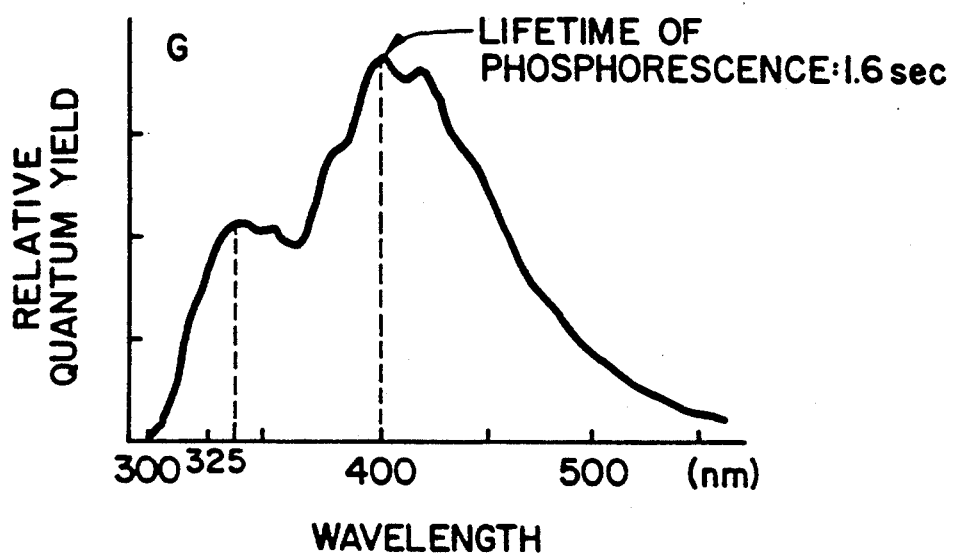
Figure 3D:
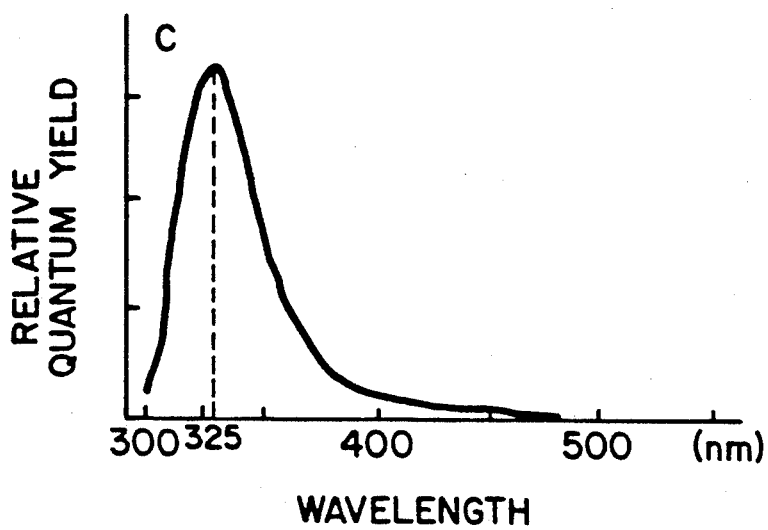
Figure 4A:
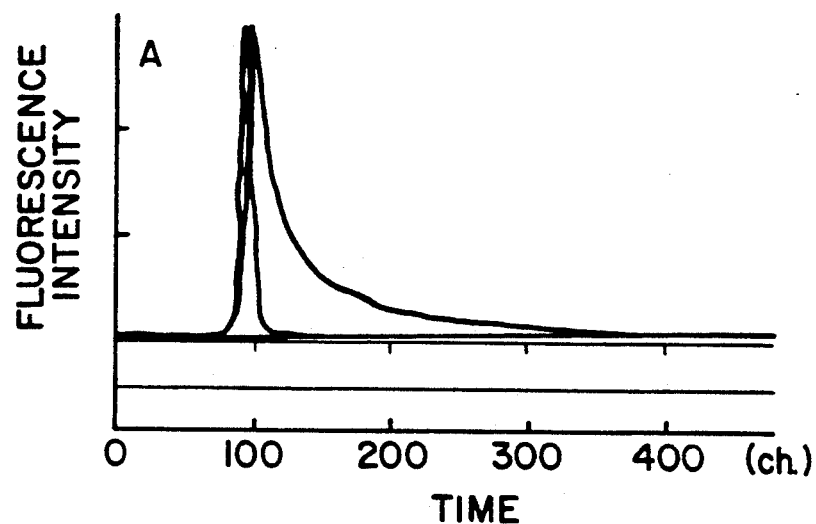
FIGS. 4A–4D are fluorescence decay curves without the addition of a (n,$\pi^*$) quencher.
Figure 4B:
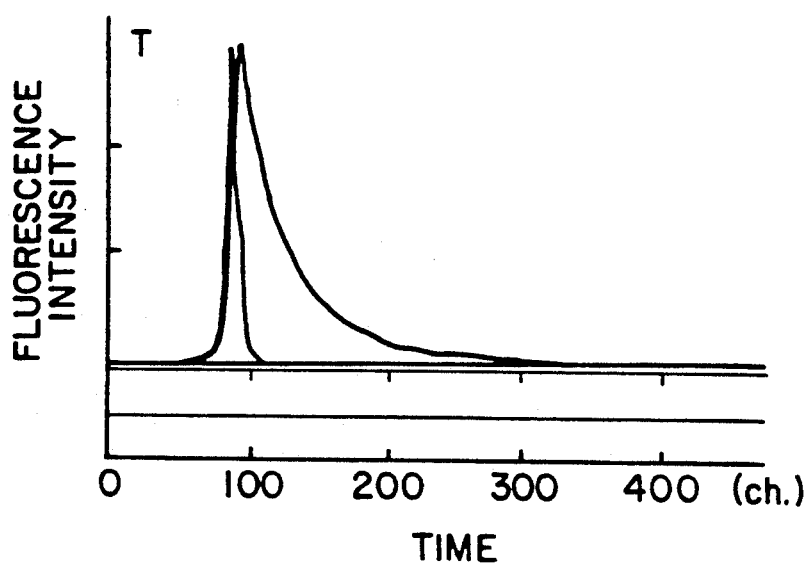
Figure 4C:
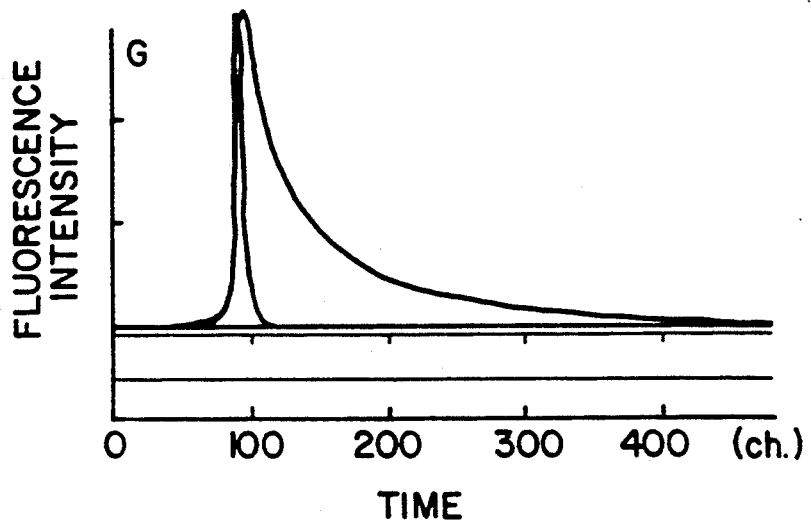
Figure 4D:
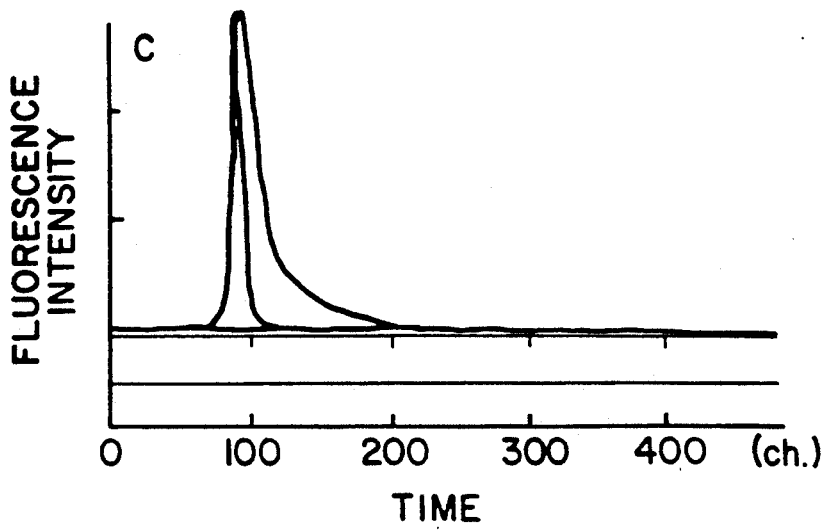
Figure 6A:
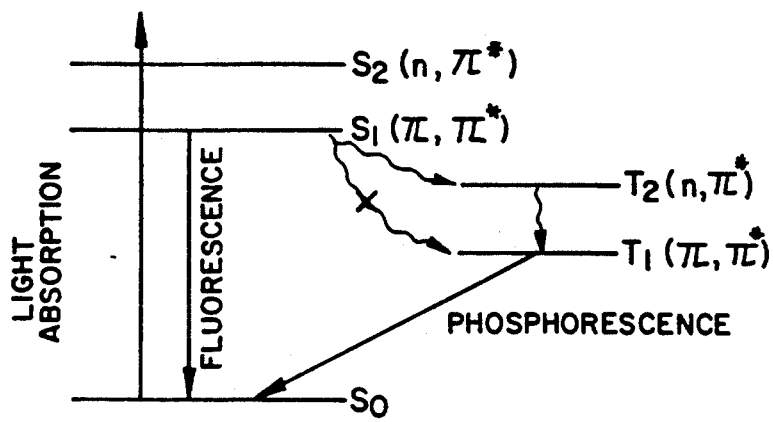
FIGS. 6A–6C are schematic energy diagrams of nucleic acid bases to illustrate fluorescence and phosphorescence properties.
Figure 6B:
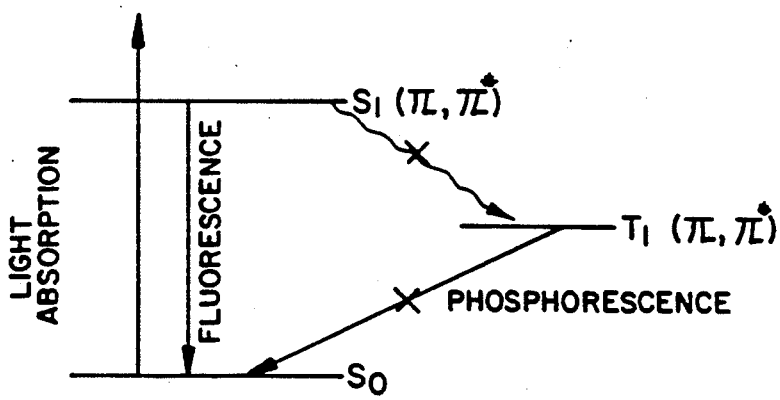
Figure 6C:
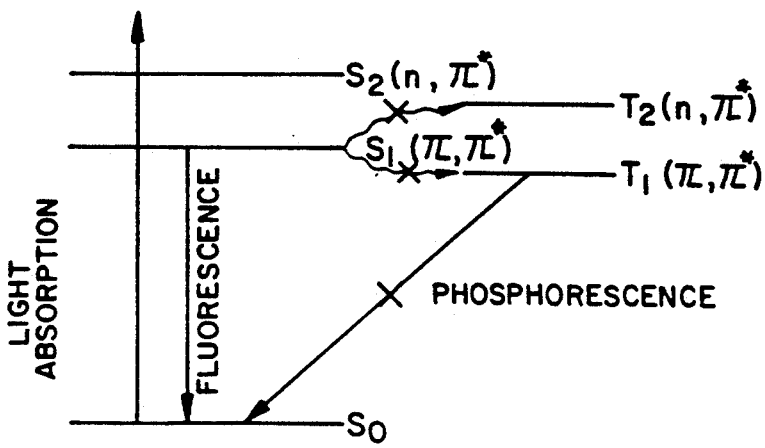
Figure 8A:
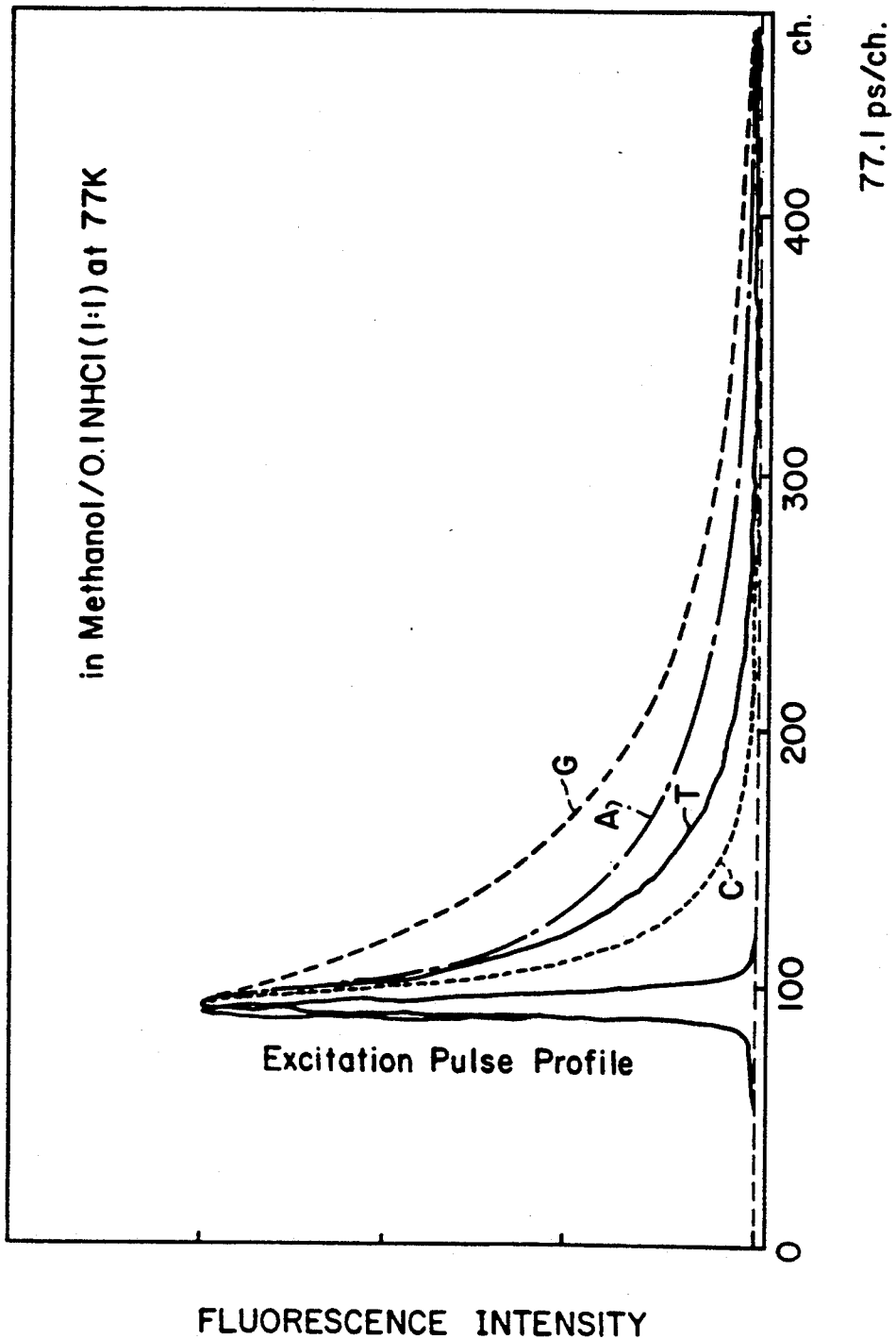
FIG. 8A shows fluorescence decay curves obtained by the method for discriminating nucleic acid bases according to this invention.

FIG. 8A shows the fluorescence decay curves with the irradiation of UV to the four samples obtained by the above method, that is, in the samples, where 0.1N hydrochloric acid is added. On the contrary, FIG. 8B shows the fluorescence decay curves of the samples including each of DNA bases but to which hydrochloric acid was not added as a $(n, \pi^*)$ quencher. In FIGS. 8A and 8B, fluorescence intensity is taken on the vertical axis, and time is taken on the horizontal axis. 1 ch of the horizontal axis is equal to 77 psec. A peak appearing at about 100 ch indicates exciting light pulse, and the decay curves came from fluorescence from the nucleic acid bases. As seen from these views, the respective nucleic acid bases have different decay curves, and there are differences in the fluorescence lifetimes. As shown in comparison of FIG. 8A with FIG. 8B, by the addition of 0.1N hydrochloric acid, the discrimination of four kinds of DNA bases becomes easier using fluorescence lifetimes. As a result, of the above method high speed and accurate discrimination can be realized.

FIG. 9A shows the relationships between these fluorescence lifetimes and ratios of the lifetime components, and FIG. 9B shows average fluorescence lifetimes of four samples, respectively, including each of four kinds of nucleic acid bases therein. As seen in FIG. 9A and 9B, it is possible to discriminate the four kinds of nucleic acid bases from one another without pretreatment, based on the ratios of the lifetime components or average fluorescence lifetimes. In particular, FIG. 9B shows the comparison between the average lifetimes of fluorescence in the samples to which 0.1N hydrochloric acid is added to samples to which quencher is not added. As shown in FIG. 9B, in the samples to which 0.1N hydrochloric acid is added, the lifetimes of fluorescence in the samples can be clearly discriminated.

Figure 10B:
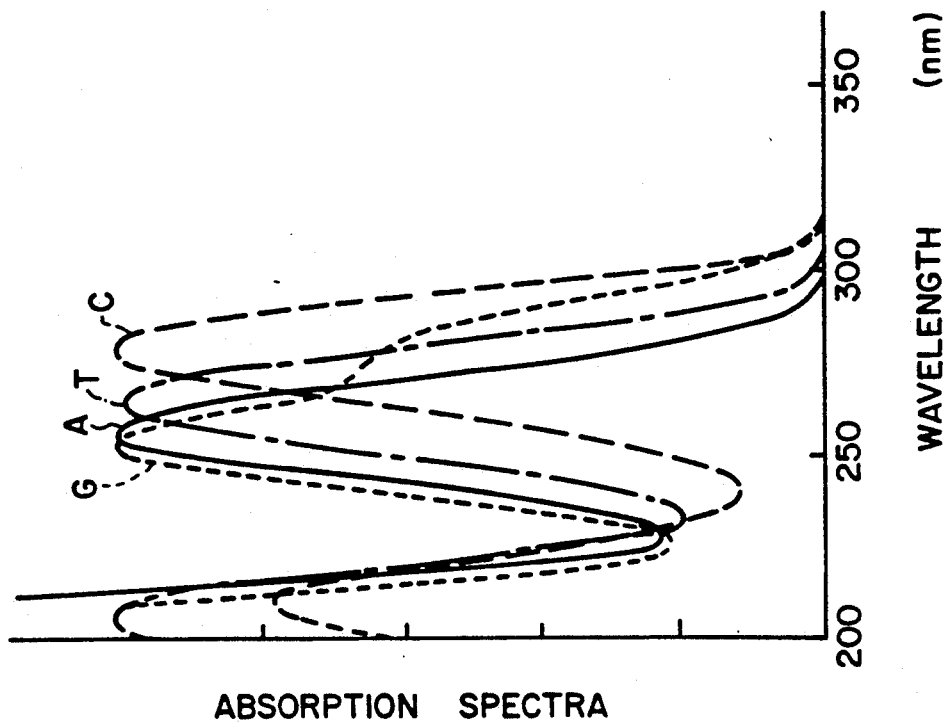
FIGS. 10A and 10B are absorption spectra with and without the addition of a (n,$\pi^*$) quencher.
Figure 10A:
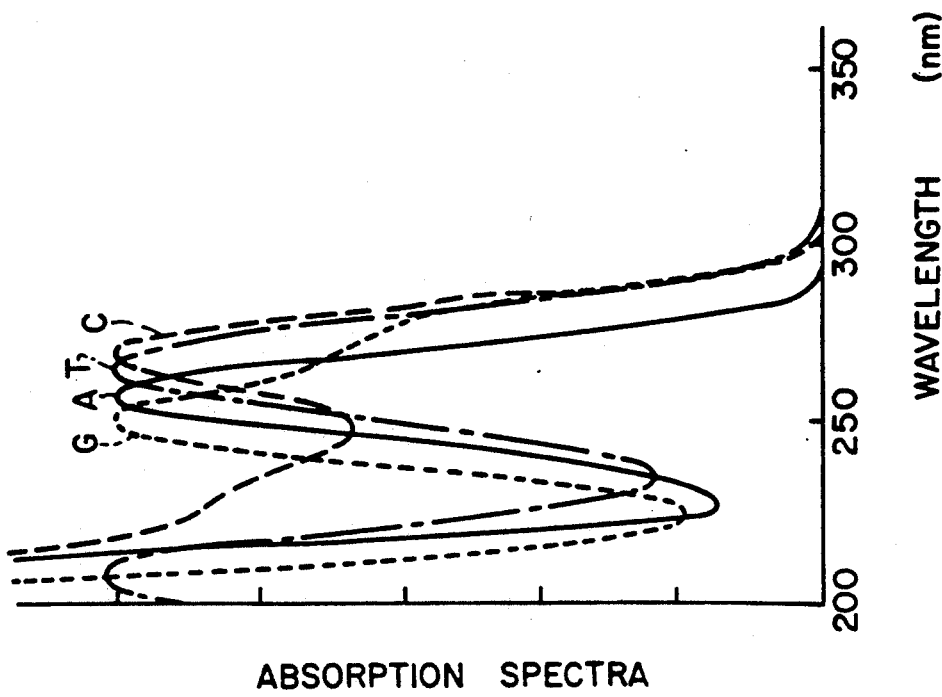

As described above, differences among the fluorescence lifetimes of nucleic acid bases A, T, G and C are made clear by the addition of a $(n, \pi^*)$ quencher. The fluorescence lifetime of G especially differs after the addition of the $(n, \pi^*)$ quencher. This could be due to differences in the reactivity of the nucleic acid bases toward H+s of the $(n, \pi^*)$ quencher. The effect of the $(n, \pi^*)$ quencher is enhancement of the fluorescence vitreous to phosphorescence with a result that differences are produced in the fluorescence lifetimes among the bases. These results are accompanied by absorption spectra of the four kinds of bases (FIG. 10).

The discriminating method based on fluorescence lifetimes of the four kinds of nucleic acid bases which is enabled by the addition of a $(n, \pi^*)$ quencher has been described above.

In this embodiment, the $(n, \pi^*)$ quencher was provided by hydrochloric acid. The effect of the addition of the quencher possibly derives from the fact that H+s are combined (protonized) with non-bonding electron pairs in carbonyl groups and in nitrogen contained in the aromatic rings, which are contained in all of A, T, G and C. Accordingly the quencher is not limited to hydrochloric acid, and acids (e.g., hydrochloric acid, sulfuric acid and nitric acid) which can protonize non-bonding electron pairs could be used. But the acids (e.g., trichloroacetic acid) having absorption spectra in a wavelength range (250~290 nm) of the excitation light are not suitable. It is necessary that the solvent can sufficiently dissolve samples, and is glassy at low temperatures. In solutions without such properties, when frozen at low temperatures, the solvent itself forms fine crystals in white powder which does not easily transmit light. In the case that samples are polar molecules, polar solvents which well dissolve the sample are preferred. Such as mixed solutions of water and alcohols (e.g., methanol, ethanol, ethylene glycol, isopropanol) of arbitrary mixing ratios. The alcohol alone, and solutions of these alcohols and ether or ketone of arbitrary mixing ratios are widely used. That is, it is necessary that components mix well with each other to form random liquid structures.

As described above, the addition of a fluorescence intensifier, such as hydrochloric acid, to the solvent makes differences in fluorescence lifetime among the four kinds of nucleic acid bases A, T, G, and C quite clear. By comparing fluorescence lifetimes of A, T, G and C observed based on their differences, A, T, G and C could be discriminated from one another at ultra-high speed. Furthermore, by suitable selection of wavelengths of the excitation light (see FIG. 10A and 10B, where separation of the peak wavelengths is noticeable when an $(n, \pi^*)$ quencher is added), as long as these bases have sufficient numbers of molecules, these bases can be accurately discriminated from one another by the measurements of the fluorescence lifetimes and those of the four kinds of nucleic acid bases.

Furthermore, the fluorescence can be intensified by the extinguishing $(n,\pi^*)$ state, which contributes to the high speed discrimination of the nucleic acid bases.

Although the above embodiments described four kinds of samples including a large number of molecules, the present invention can be applied to the discrimination of single-molecule samples.

From the invention thus described, it will be obvious that the invention could be varied in many ways. Such variations are not to be regarded as a departure from the spirit and scope of the invention, and all such modifications as would be obvious to one skilled in the art are intended to be included within the scope of the following claims.

I claim:

1. A method for discriminating four kinds of nucleic acid bases of DNA, adenine, thymine, guanine and cytosine, comprising the steps of:

adding a sample to a polar vitreous solvent to form a glassy solution, said polar vitreous solvent comprising a polar solvent selected from the group consisting of alcohol, a mixed liquid of alcohol and water in an arbitrary mixing ratio, and a mixed liquid of alcohol and ether or ketone in an arbitrary mixing ratio;

reducing the temperature of the glassy solution;

adding an $(n,\pi^*)$ quencher comprising a strong acid as a fluorescence intensifying agent to the solution;

irradiating an excitation light of UV laser beams thereto;

measuring the lifetime of fluorescence from the sample; and discriminating the kind of the nucleic acid base of DNA included in the sample, based on the lifetime of the fluorescence from the sample.

2. A method according to claim 1, wherein said an $(n,\pi^*)$ quencher is a strong acid having no absorption spectrum in the wavelength region of the excitation light of 250-290 nm.

3. A method according to claim 2, wherein said strong acid is 0.1N hydrochloric acid.

4. A method according to claim 1, wherein the kind of the nucleic acid base is discriminated based on average fluorescence lifetime of the sample.

* * * * *